United States Patent [19]
Baron et al.

[11] Patent Number: 5,688,282
[45] Date of Patent: Nov. 18, 1997

[54] DISTRACTION APPARATUS FOR A KNEE

[75] Inventors: Lionel Baron, Oistreham; Patrick Schifrine, Veyrier du Lac; Denis Van de Velde, Valenciennes; Nicolas Moncade, Echau; Louis Setiey, Gleize; Philippe Segal, Cormontreuil; Marc Raguet, Chalons S/Marne; Claude Vielpeau, Hérouville-Saint-Clair; Bruno Balay, Saint Bernard; Jean-Marie François, Marienthal; Philippe Stahl, Sainghain en Melantois; Michel Serrault, Flers; Paul Rivat, Saint Peray; Didier Mailhe, Castelnau le Lez, all of France; Vittorio Monteleone, Napoli, Italy; Jean-Marie Verleyen, Grigny, France

[73] Assignee: Benois & Girard & Cie, Hérouville-Saint-Clair, France

[21] Appl. No.: 689,976

[22] Filed: Aug. 16, 1996

[30] Foreign Application Priority Data

Aug. 24, 1995 [FR] France ................... 95 10055

[51] Int. Cl.6 .................... A61B 17/60; A61F 5/00
[52] U.S. Cl. .................... 606/90; 606/87; 606/88
[58] Field of Search .................... 606/90, 88, 87, 606/89

[56] References Cited

U.S. PATENT DOCUMENTS

| | | | |
|---|---|---|---|
| 4,501,266 | 2/1985 | McDaniel | 128/69 |
| 4,566,448 | 1/1986 | Rohr | 128/92 |
| 4,653,488 | 3/1987 | Kenna et al. | 606/88 |
| 5,116,338 | 5/1992 | Poggie et al. | 606/90 |
| 5,213,112 | 5/1993 | Niwa et al. | 606/90 |
| 5,468,244 | 11/1995 | Attfield et al. | 606/90 |

FOREIGN PATENT DOCUMENTS

| | | |
|---|---|---|
| 2648699A1 | 12/1990 | France . |
| 9301611U1 | 6/1993 | Germany . |

OTHER PUBLICATIONS

"Total Knee-Replacement Arthroplasty", Journal of Bone & Joint Surgery, vol. 65a., No. 3, Mar. 1983, pp. 293–309, by N.S. Effekhar.

*Primary Examiner*—Michael Buiz
*Assistant Examiner*—Julian W. Woo
*Attorney, Agent, or Firm*—Peter C. Richardson; Lawrence C. Akers; Raymond W. Augustin

[57] ABSTRACT

A space correction apparatus is provided for a knee prosthesis comprising a body and two pairs of parallel runners extending on both sides of the body in a direction perpendicular to the plane of the body and of which the spacing of the front and back parts can be adjusted independently. This apparatus makes it possible to measure the spacing between the resected parts of the tibia and the femur in the extension position and to reproduce the spacing in flexion position so as to perform resections of the femur in this latter position.

16 Claims, 16 Drawing Sheets

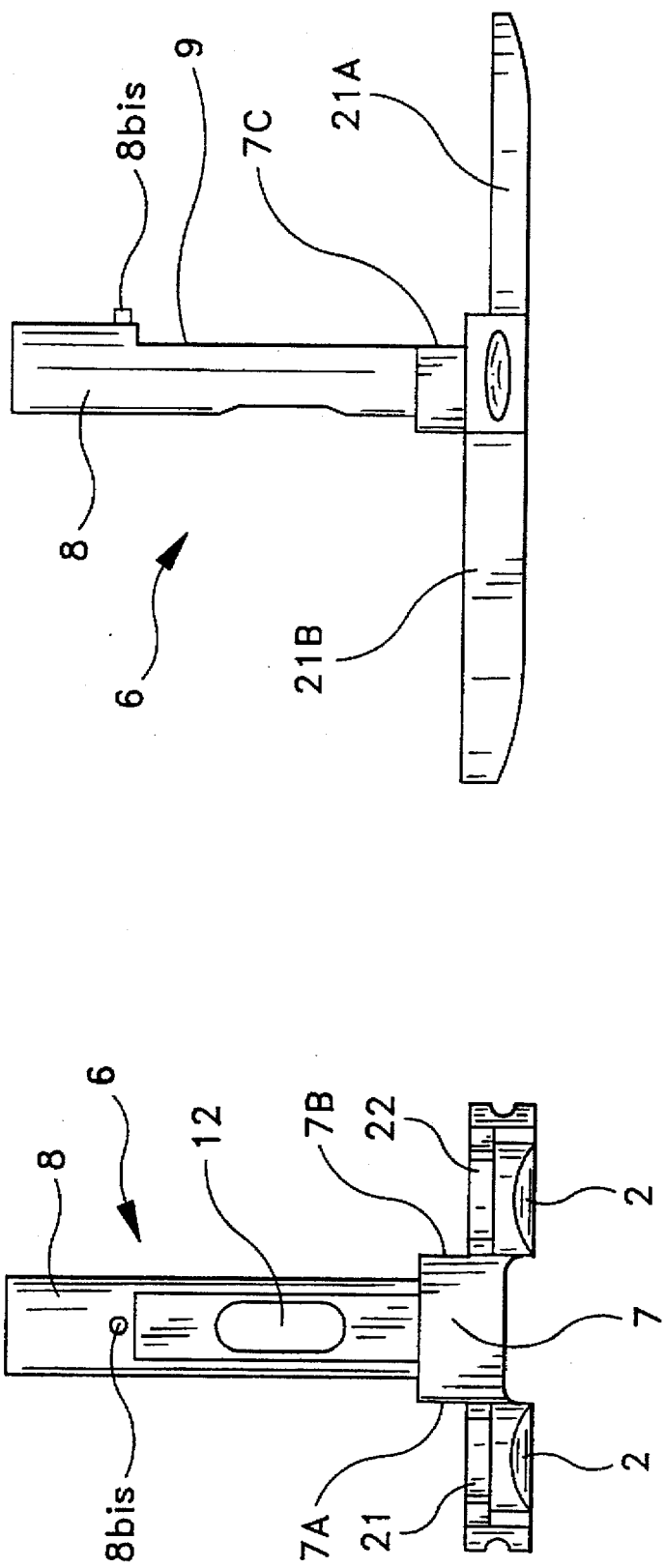

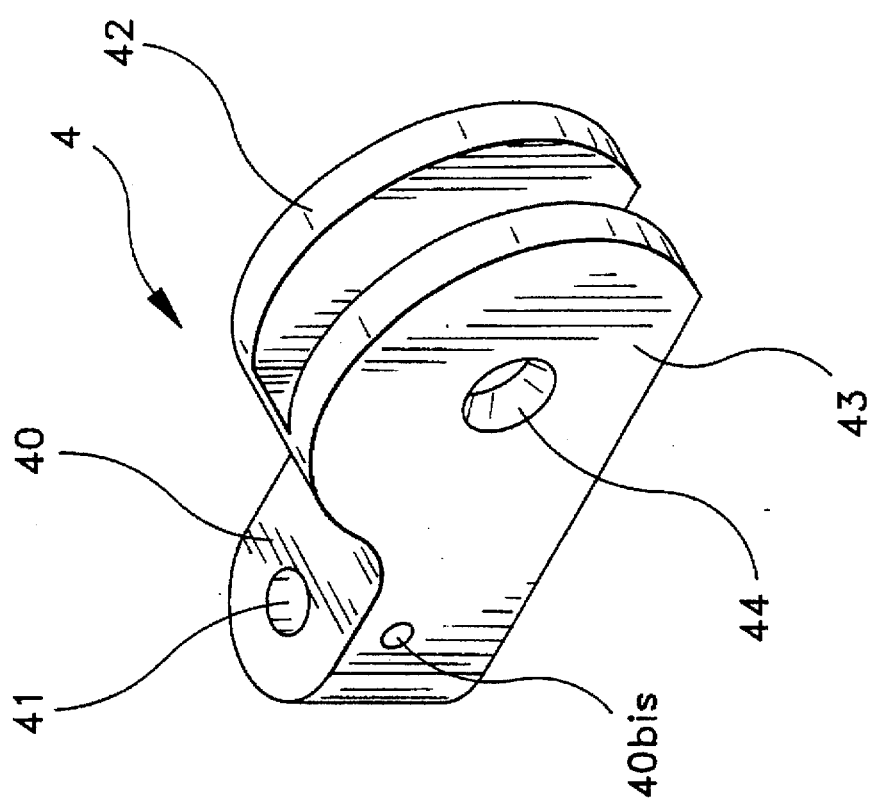
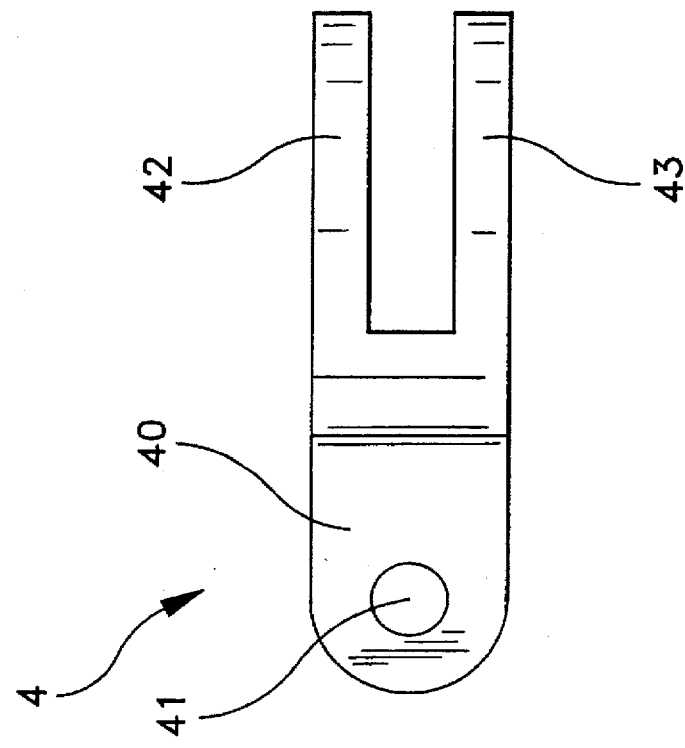

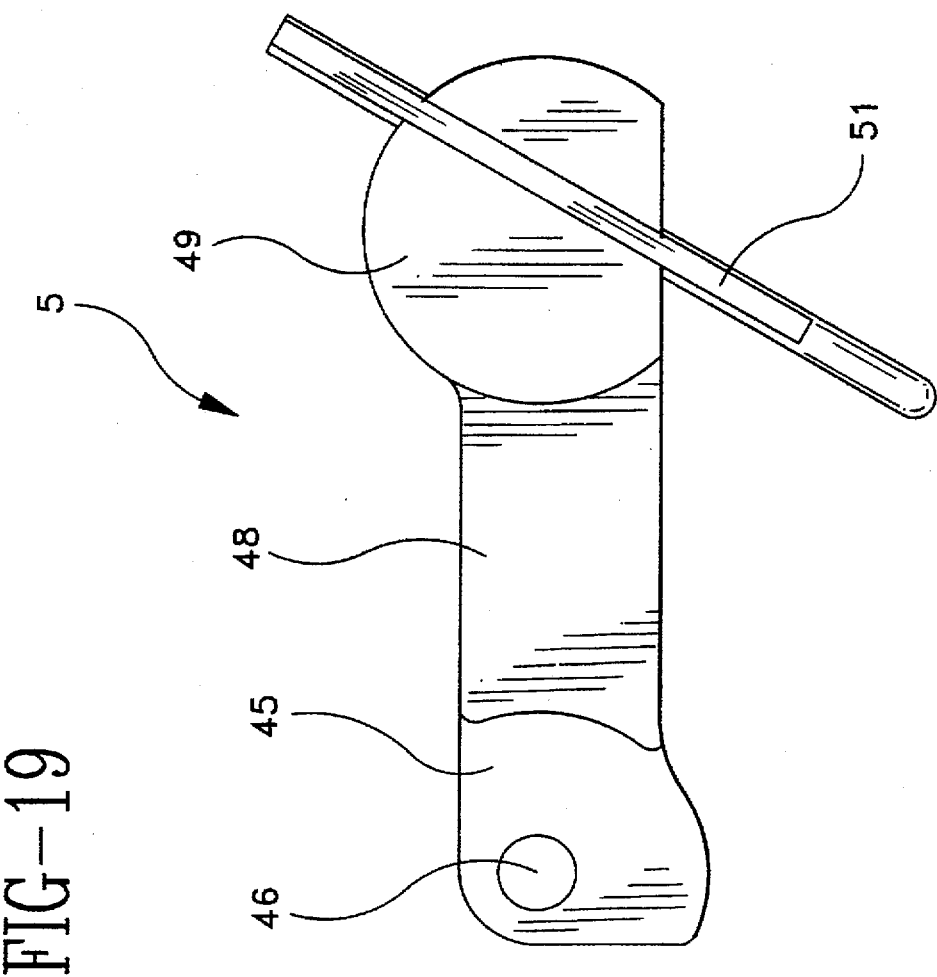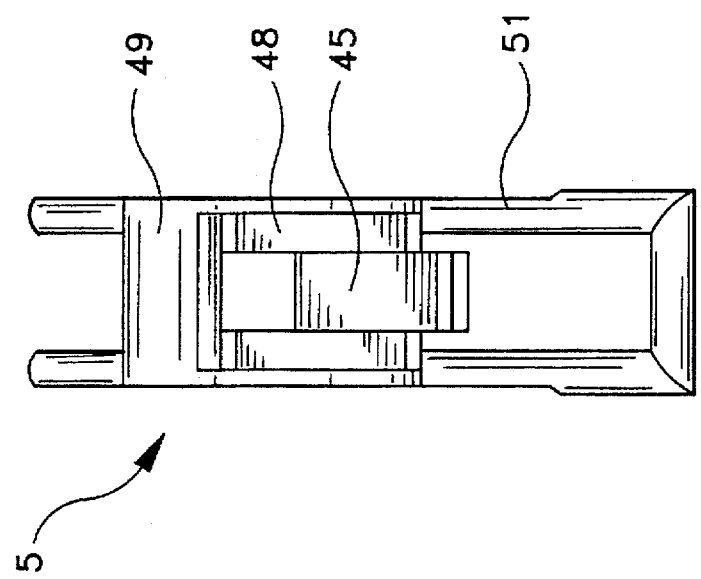

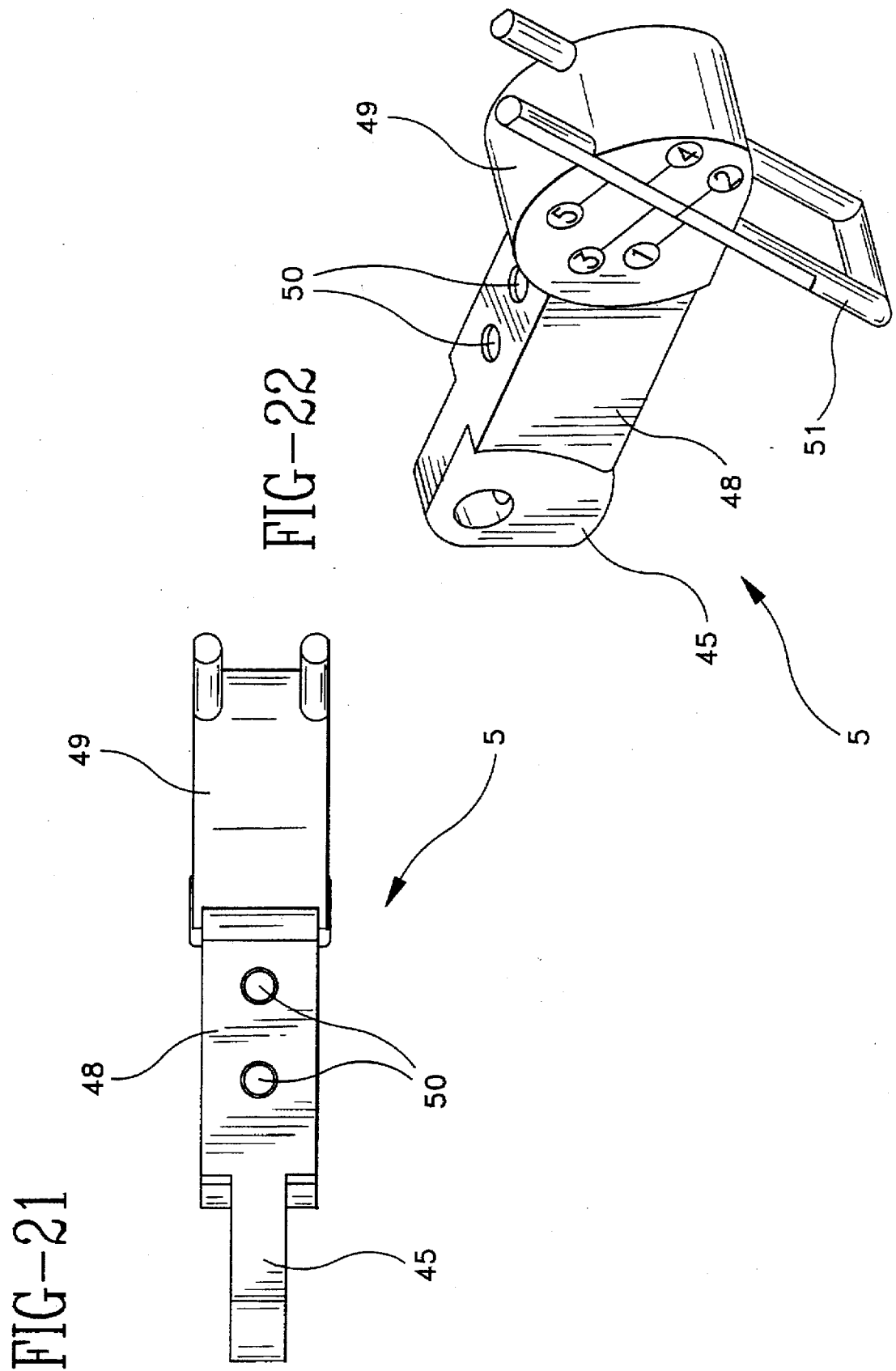

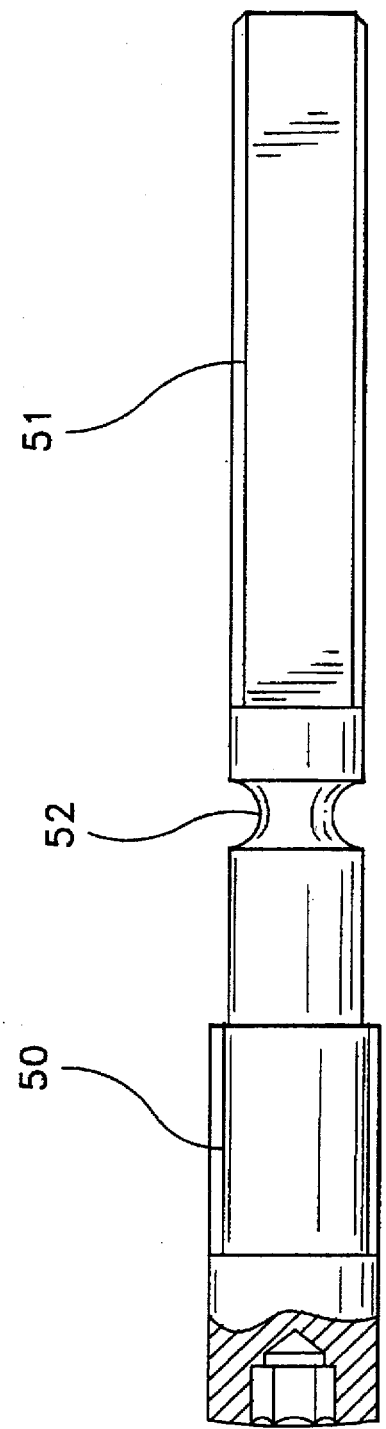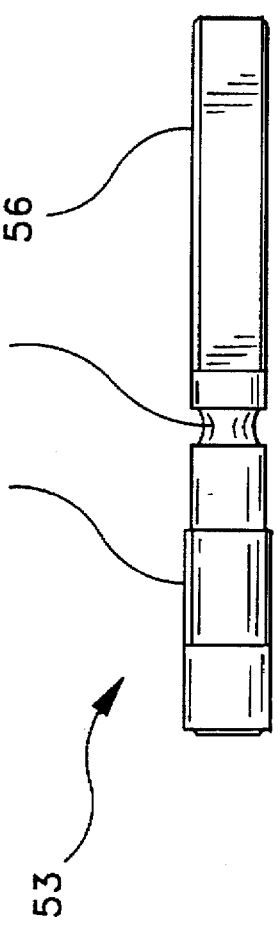

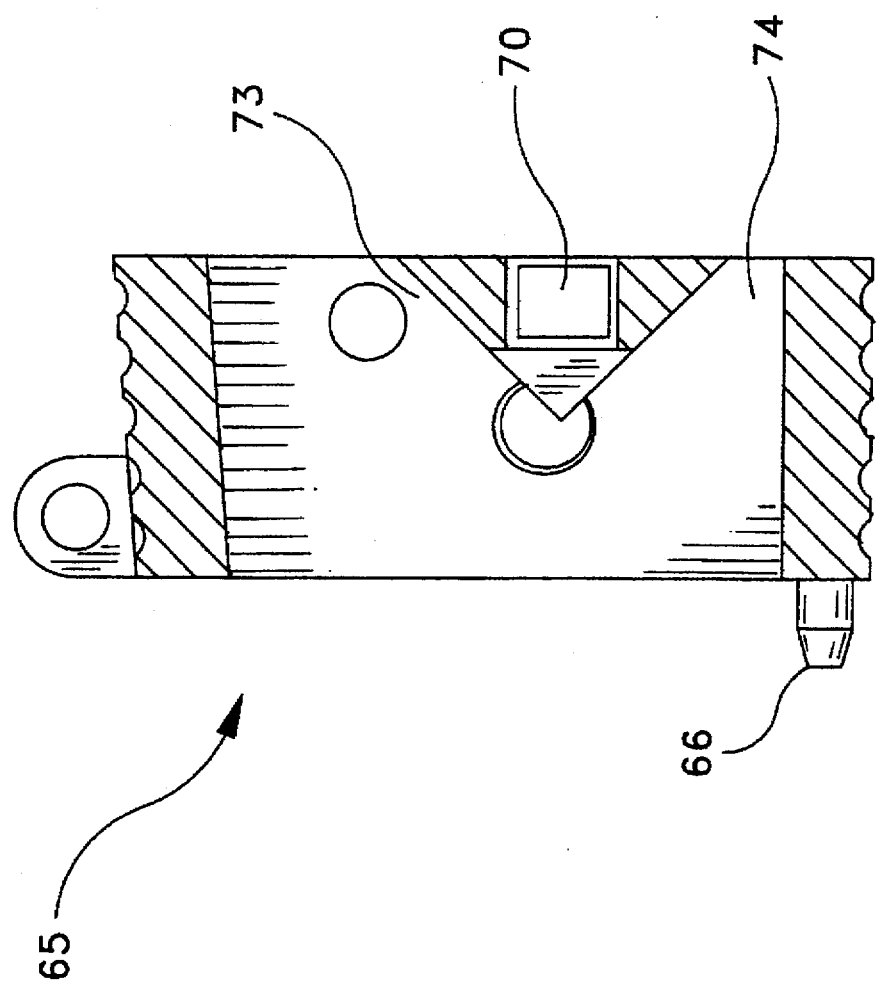

DISTRACTION APPARATUS FOR A KNEE

BACKGROUND OF THE INVENTION

1. Field of the Invention

This invention relates to a distraction instrument used to balance the ligaments during a total knee replacement surgery.

2. Description of the Prior Art

A conventional knee prosthesis usually comprises a tibial element implanted on a resection plane formed on the bone of the proximal upper part of the tibia, an intermediate meniscus, and a femoral component with two condyles requiring for its implantation in the distal lower part of the femur three resection planes. One plane corresponds to the extension position and the other two planes to the flexion position, as well as one, or perhaps two, chamfers each at approximately 45° planes on either side of the resection plane of the femur corresponding to the position of extension.

To be able to implant such a knee prosthesis, the proximal upper part of the tibia and the distal lower part of the femur must be resected, so that the same distance is preserved between the resection planes of these two bones, in both the extension position of the leg (corresponding to the standing position of the patient) and the flexion position of the leg (corresponding to the sitting position).

To respect this condition and make it possible to implant the prosthesis, it is necessary to measure the precise distance between the cutting planes of the tibia and of the femur in position of extension by selecting a given balanced ligament tension and to carry this distance over in position of flexion in order to determine the second and third femur resection planes, which in practice are very close to the orthogonal in relation to the first resection plane of the femur, and to execute at least one and preferably two chamfers in planes inclined at an angle of approximately 45° in relation to the said resection planes of the distal extremity of the femur, as defined above.

SUMMARY OF THE INVENTION

The object of the present invention is to provide an apparatus that will enable the surgeon to adjust the space between the proximal resection plane of the tibia and the distal resection plane of the femur in the extension position and to determine the second cutting (or resection) plane or planes of the femur in the flexion position, and if necessary, the cutting planes of the chamfers, while respecting the previously determined spacing.

The space correction apparatus for knee prosthesis according to the invention comprises a body having parallel front and rear surfaces and two pairs of runners, arranged one above the other, all parallel to each other and extending, in a plane perpendicular to the front and rear surfaces, beyond the rear surface so as to form rear parts, and forward of the front surface of the body, so as to form front parts. The front and rear parts of the lower pair of runners are integral with one another and can be moved simultaneously in relation to the body and the front and rear parts of the upper pair of runners are not integral. The front parts of the upper pair of runners can be moved individually in relation to the body, and the rear parts of the upper pair of runners are both integral with the body.

The body is provided with a calibration arm attached to the body in such as way as to pivot around an axis perpendicular to the front and rear surfaces and preferably comprising a device for measuring the size of the femoral element and it can be provided with a detachable anterior-posterior (universally) cutting guide, which can be attached to the body in a specific position.

The apparatus according to the invention is used in surgery as follows:

Following resection of the tibial proximal extremity and the distal femoral extremity in the extension position, the surgeon introduces between the resection planes and the rear (extension) parts of the two pairs of runners or skids of the apparatus, which have previously been brought into contact with one another. He then separates the two pairs of runners from each other until their abutment on the resected planes, in order to obtain the spacing to be carried over to the flexion position.

The surgeon then balances the lateral ligament tension in this position where the rear part of the upper pair of runners is in contact with the resection site of the distal condyle of the femur and verifies the hip-knee-ankle alignment by means of a longitudinal rod threaded in the calibration arm. In other words, the alignment of the rod with the femorotibial anatomical axis of the patient runs from the center of the femoral head to the center of the ankle.

After removing the apparatus and attaching the antero-posterior cutting guide on the body, the surgeon introduces the front (flexion) parts of the two pairs of runners of the apparatus between the tibia and femur in position of flexion, then carries over the spacing obtained in the extension position, and can then, if necessary, individually move the front part of one or the other of the runners of the upper pair in order to cause the femur to turn and thus place the ligaments under tension, which stabilizes and recenters the patella.

The cutting guide, whose position on the body and shape determines the anterior and posterior cutting planes of the femur in the flexion position, is then attached to the distal resected part of the femur by any appropriate means; the guide is disconnected from the apparatus and the surgeon can then create with a saw the anterior and posterior cutting planes of the femur, which in practice are orthogonal to the resected distal part of the femur as well as the one or two chamfers required for implantation of the femoral component of the prosthesis.

The choice of the size of this femoral element is facilitated by the size-measuring device.

These and other objects and advantages of the present invention will become apparent from the following description of the accompanying drawings, which disclose several embodiments of the invention. It is to be understood that the drawings are to be used for the purposes of illustration only and not as a definition of the invention.

BRIEF DESCRIPTION OF THE DRAWINGS

In the drawings, wherein similar reference characters denote similar elements throughout the several views:

FIGS. 2, 3, 4 and 5 represent, respectively, a side view, front view, top view and view in perspective of the body of the apparatus according to FIG. 1;

FIGS. 15, 16, 17 and 18 represent, respectively, a cutaway front view along line CC of FIG. 16, a side view, top view and view in perspective of a support for the calibration arm, with a device for measuring the size of the prosthetic femoral element of FIG. 1;

FIGS. 19 to 22 represent, respectively, a side view, front view, top view and a view in perspective of the calibration arm comprising a device for measuring the size of the femoral element of the knee prosthesis;

FIGS. 23 and 24 represent, respectively, a central maneuvering screw for the lower pair of runners and a lateral adjustment screw for only the front part of one of the runners of the upper pair of runners on the apparatus according to the invention;

FIGS. 29 to 31 represent, respectively, views in perspective, seen lying down and upright, and a section along line EE of FIG. 29 of an anteroposterior cutting guide that can be attached to the apparatus according to the invention.

DESCRIPTION OF THE PREFERRED EMBODIMENT

Figure 1:
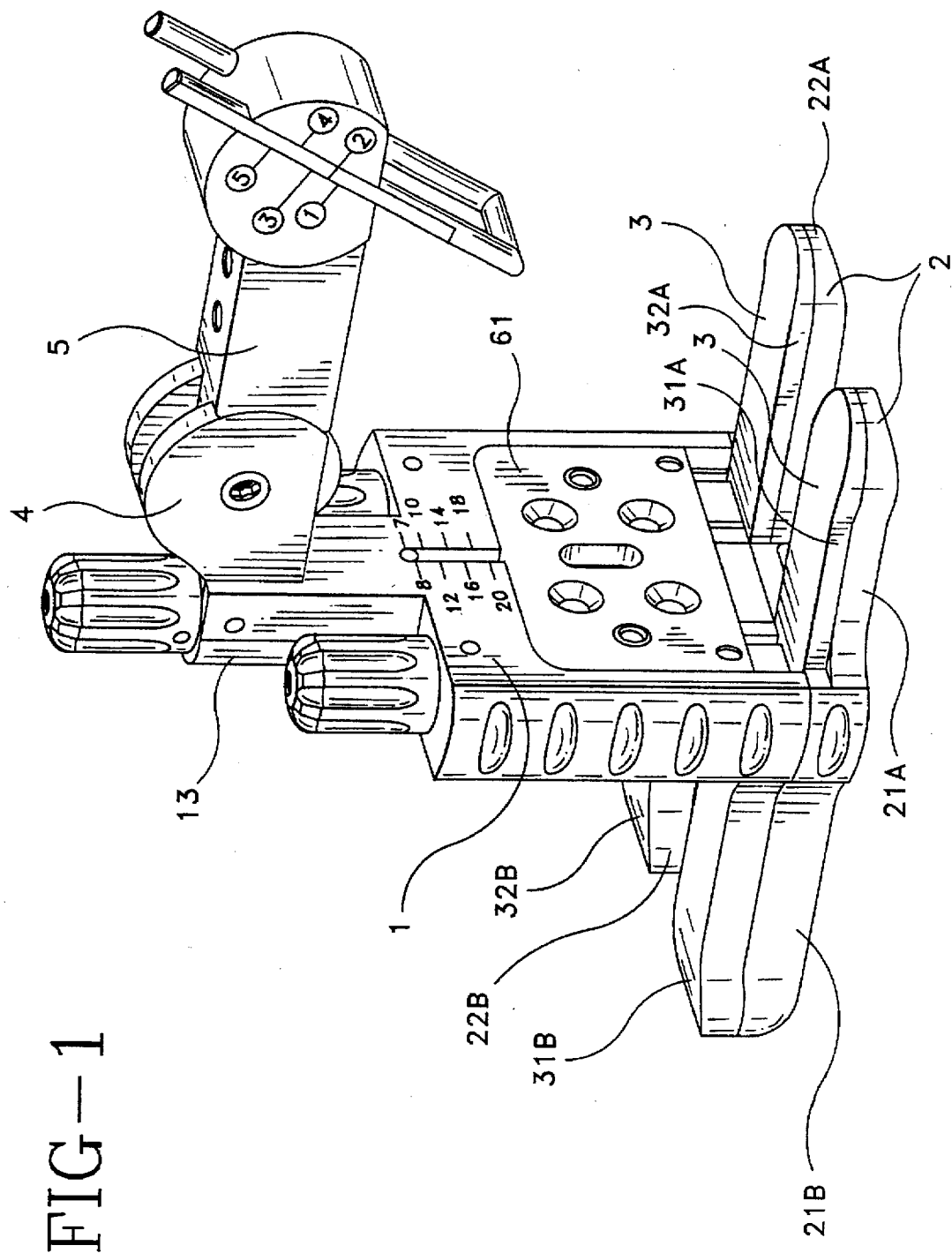
FIG. 1 represents a view in perspective of the apparatus of the present invention provided with a calibration arm having a device for measuring the size of the prosthetic femoral element.
Figure 5:
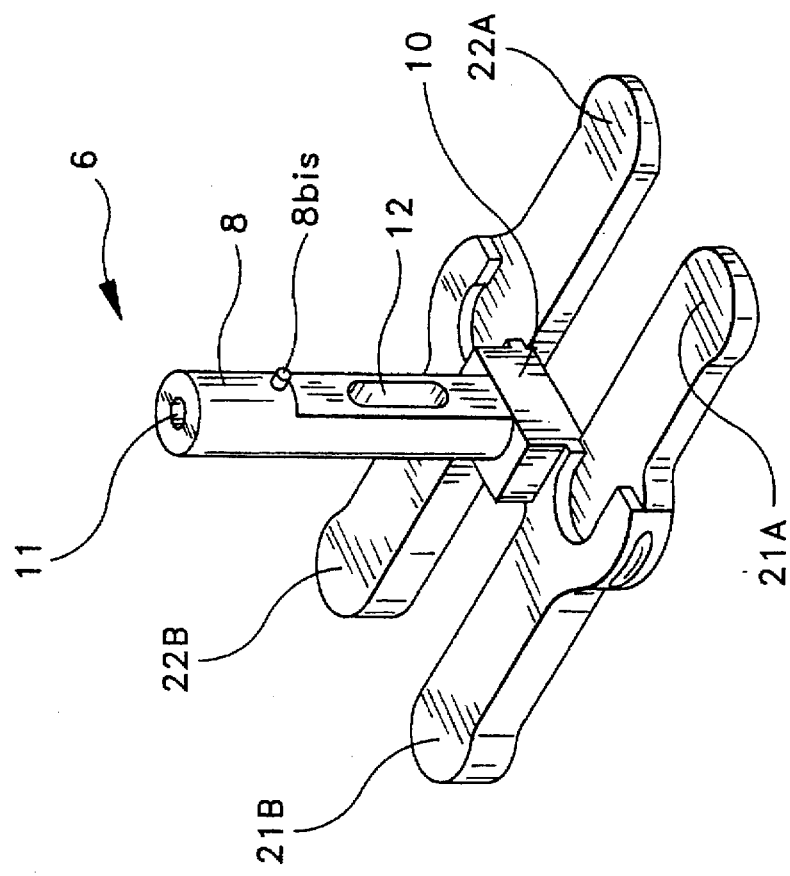
Figure 4:
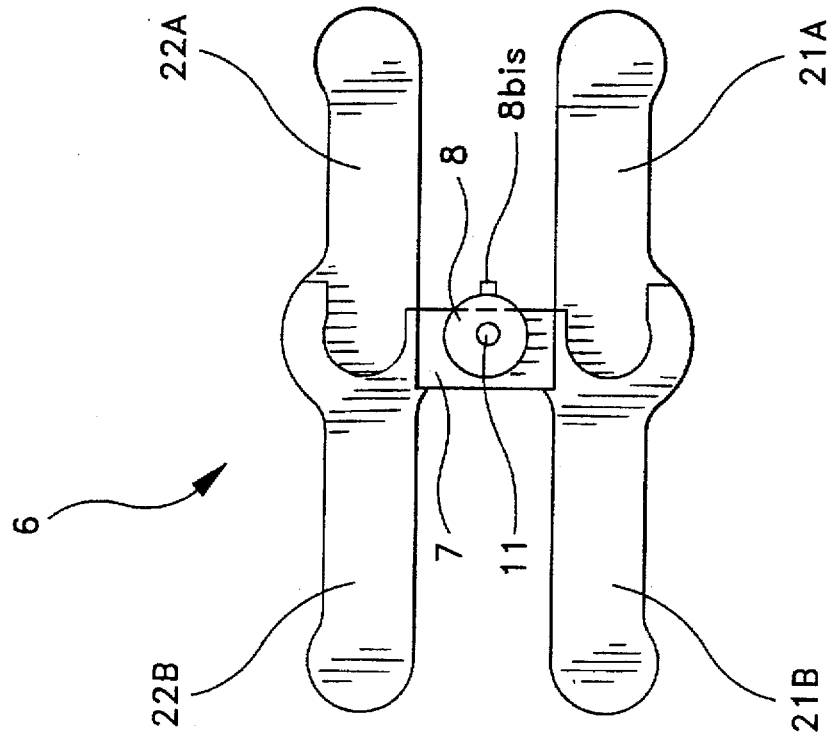

With reference to FIG. 1, the apparatus according to the invention comprises a body 1 having generally parallel front and rear surfaces and two pairs 2 and 3 of runners arranged one above the other, extending in a plane perpendicular to that of the front and rear body surfaces.

The runners of these two pairs are parallel to one another, each comprising a thicker rear part 21B, 22B and 31B, 32B located behind the plane of the rear surface of the body 1 and a thinner front part 21A, 22A and 31A, 32A located in front of the front surface of body 1 as shown in FIG. 1. runners or skids 21A, 21B, 22A and 22B are integrally formed on a distraction plate 6.

Body 1 includes three parallel bores, the vertical axes of which lie in the same plane, which defines the front and rear surfaces of body 1.

Each of these bores accepts an adjustment screw 4A surmounted by a knurled knob, the central bore also accepting a support 4 for a calibration arm 5 provided with a device for measuring the size of the femoral element and mounted on a tubular extension 13.

Moveable distraction plate 6 is shown in FIGS. 2 to 5 which includes the lower pair 2 of runners 21, 22 which are made integral with a central pillar by means of a block 7.

The block 7 has two lateral faces 7A and 7B embedded in body 1.

The central pillar 8 has a circular cross section with two parallel flat faces, of which one, having the reference number 9, lies in the same plane as the front face 7C of the block 7 and the step 10 which is due to the difference in thickness between the front parts 21A and 22A and the rear parts 21B and 22B of the runners 21 and 22.

Central pillar 8 also comprises a threaded bore 11 located along the axis of the pillar, which runs from the upper part opposite the runners and opens into an oblong hole 12, crossing right through pillar 8 from one flat side to the other (see FIG. 2).

Finally, pillar 8 has a guide pin 8B, shown in FIGS. 2 to 5, designed to cooperate with a vertical groove 27B in body 1 to show the relative displacement of these elements and to serve as cursor moving along a graduation indicating the thicknesses of the meniscus of the knee prosthesis.

Referring to FIGS. 6–10 the body 1 of the preferred apparatus according to the invention will now be described.

Body 1 is generally rectangular in shape and has a central tubular extension 13 and with the rear parts 31B and 32B of the upper pair 3 of runners 31 and 32.

Figure 7:
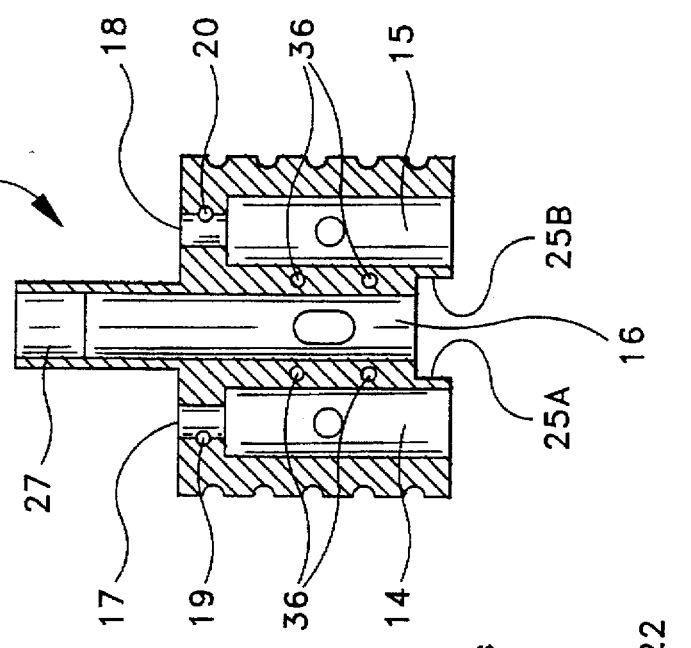
FIGS. 6, 7, 8, 9 and 10 represent, respectively, a front view, a section along line AA of FIG. 8, and a side view, top view and view in perspective of a movable portion of the apparatus according to FIG. 1.
Figure 8:
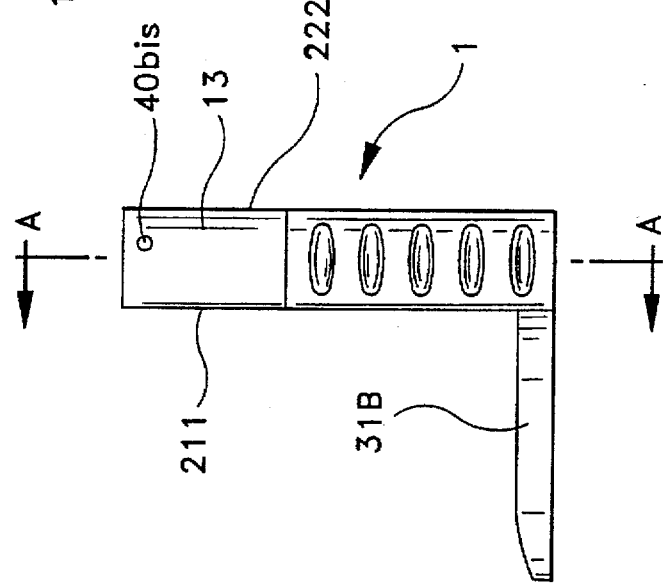
Figure 6:
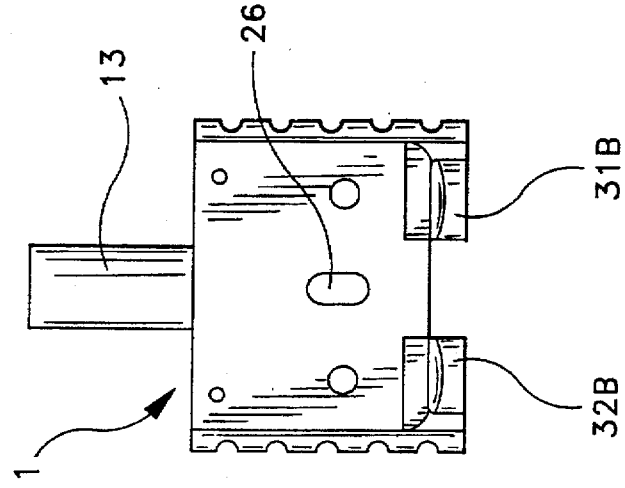

As shown in FIG. 7 in the preferred embodiment, body 1 comprises three parallel cylindrical bores: the two side bores 14 and 15 are designed to receive the guide posts of the front parts of the runners of upper pair 3 and the central bore 16 is designed to receive the central pillar 8 of the spacer 6.

The two side bores 14 and 15 are open at their lower extremity and are extended at their upper extremity by a threaded bore of smaller diameter 17 and 18 serving for passage of an adjustment screw (not shown).

Threaded bores 17 and 18 are traversed at right angles by a lateral pin 19 and 20 respectively which emerges on the surfaces 211 and 222 of body 1.

The central bore 16 comprises in its lower part recessed surfaces 25A and B which cooperate with guide surfaces 7A and 7B of block 7 of spacer 6 at its median part, an oblong hole 26 corresponding to the oblong hole 12 of spacer 6, and is extended at its upper part by a central tubular extension 13.

The central tubular extension 13 comprises a notch 27 with pin 40B for receiving and immobilizing the support 4 of calibration arm 5 with a device for measuring the size of the femoral element, as respectively illustrated in FIG. 1.

Finally, body 1 has on its front surface position means for a retaining plate and a cutting guide, which can include, for example, threaded bores 36 and a window 37 delimited by vertical side walls 38 and 39.

Figure 10:
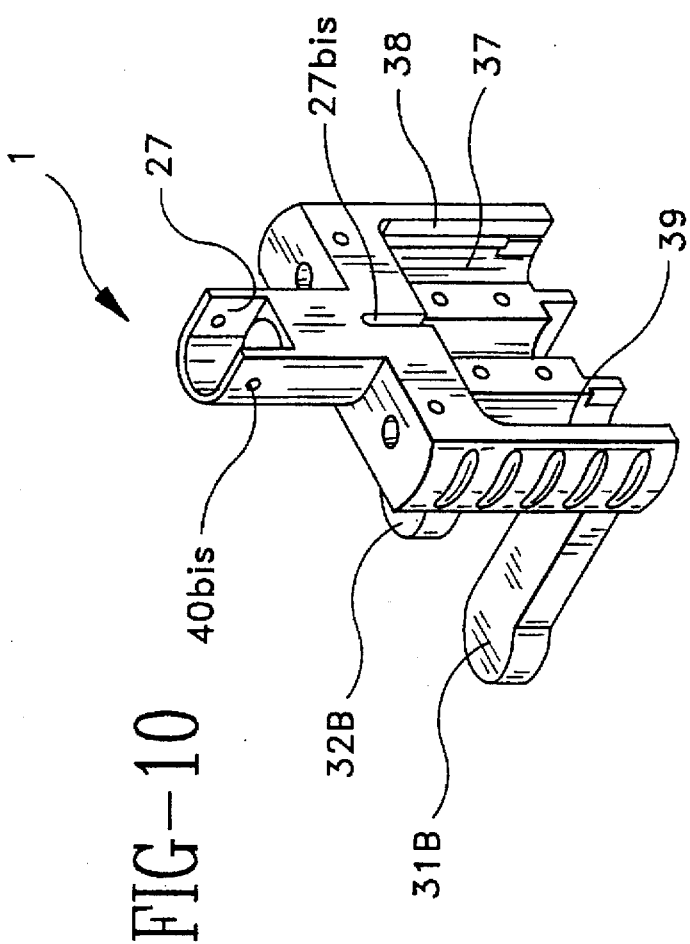
Figure 9:
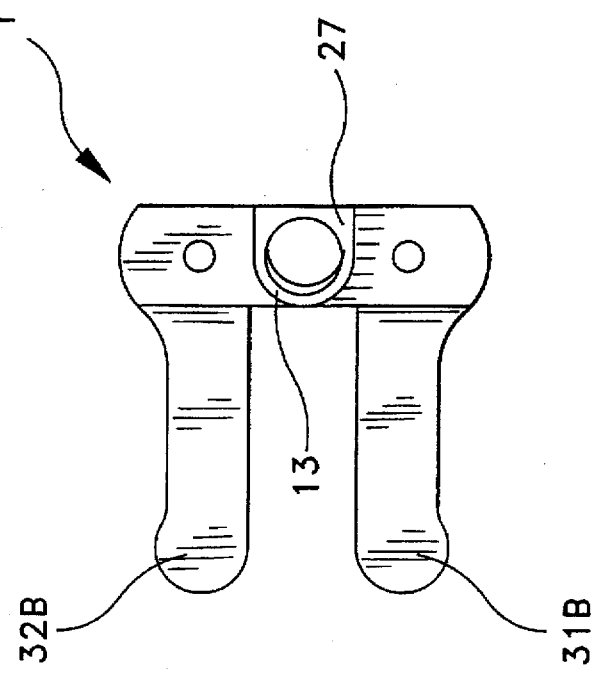
Figure 12:
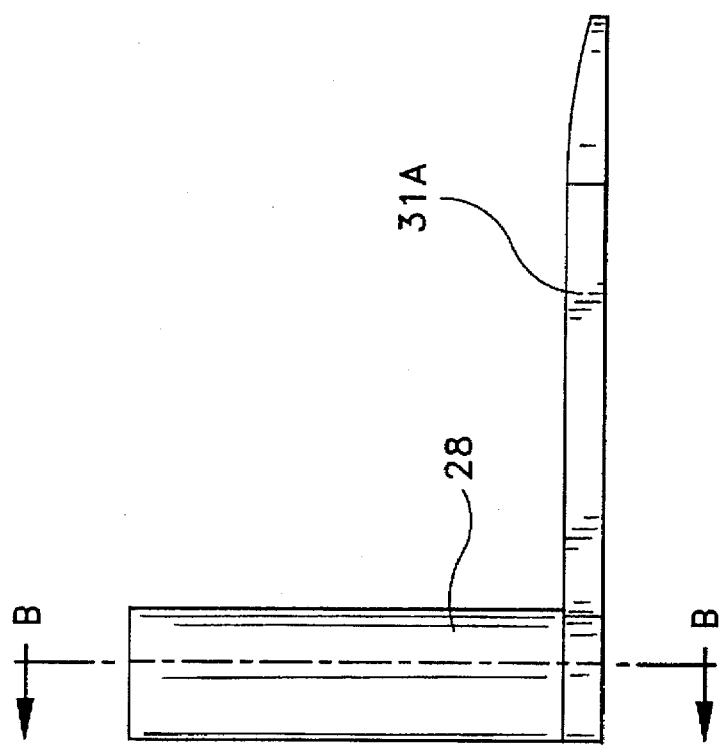
FIGS. 11, 12, 13 and 14 represent, respectively, a cutaway front view along line BB of FIG. 12, a side view, top view and view in perspective of the front part of one of the runners of the upper pair of runners.
Figure 11:
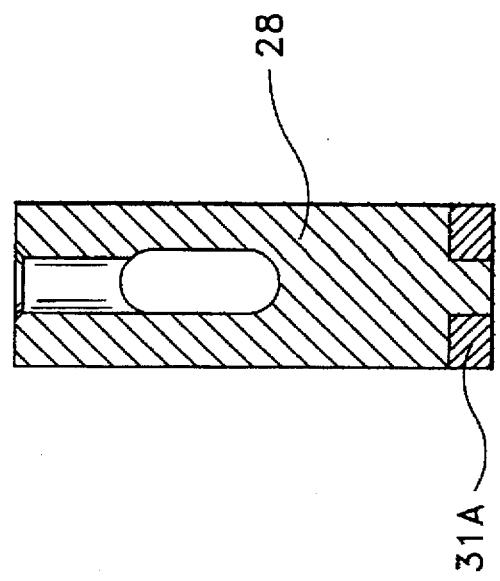
Figure 14:
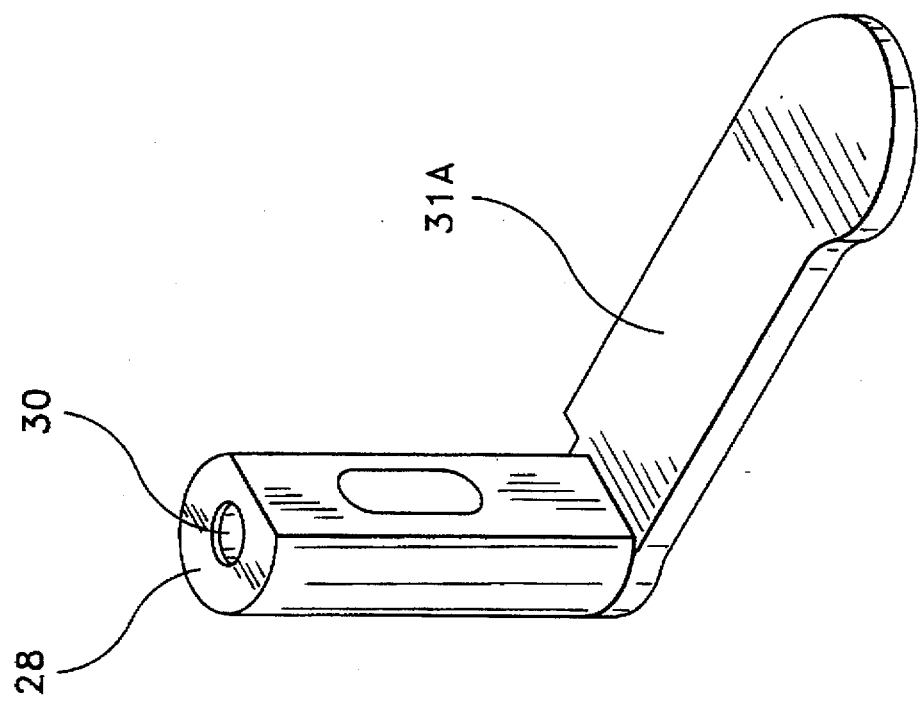
Figure 13:
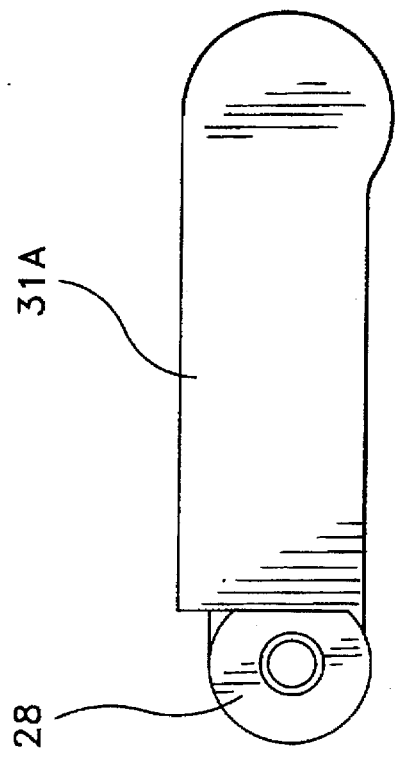
Figure 16:
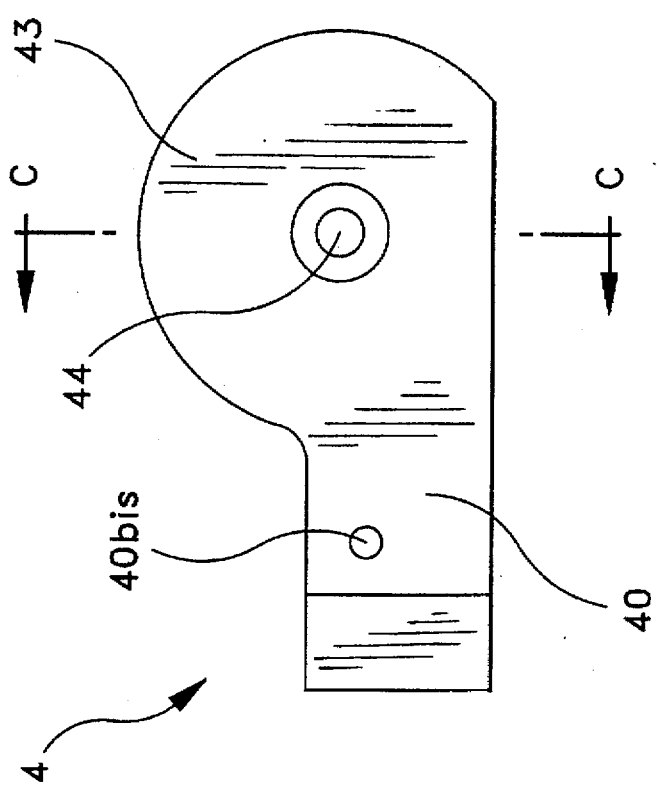
Figure 15:
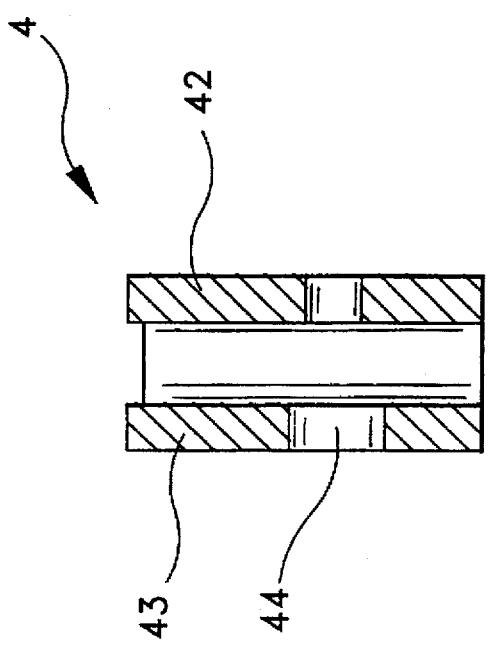
Figure 26:
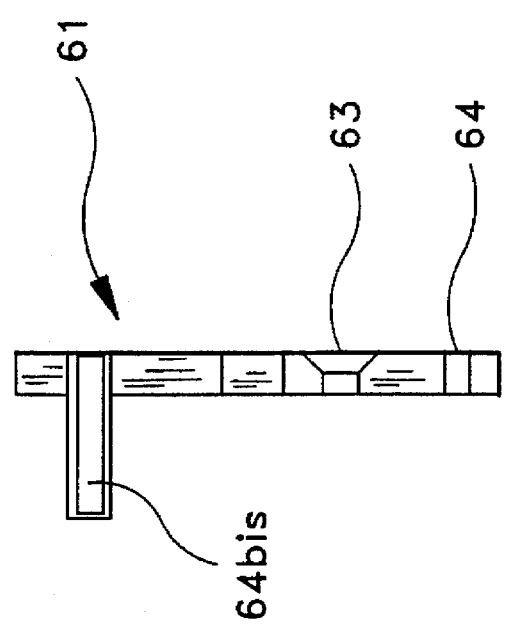
FIGS. 25 to 28 represent, respectively, a front view, side view, rear view and view in perspective of a retaining plate used with the apparatus of FIG. 1.
Figure 25:
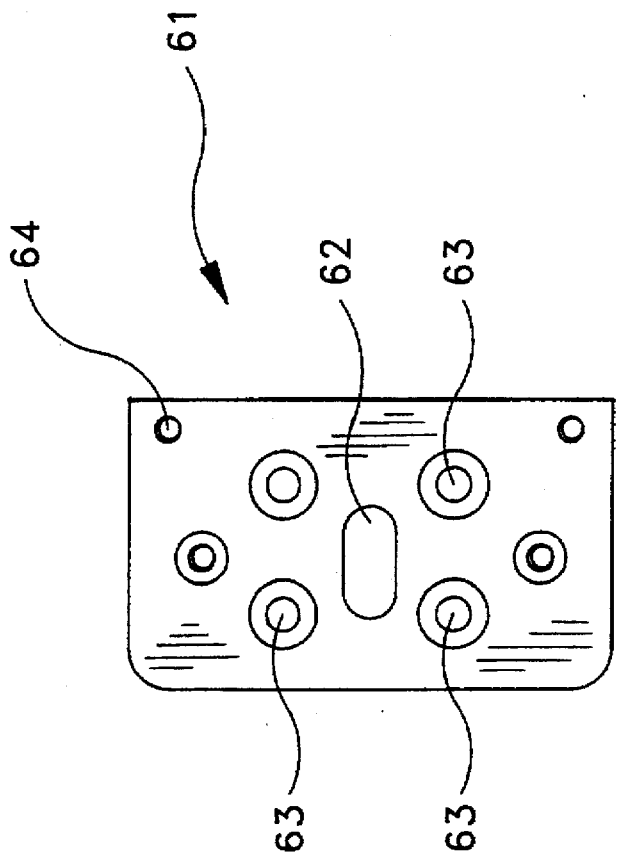
Figure 28:
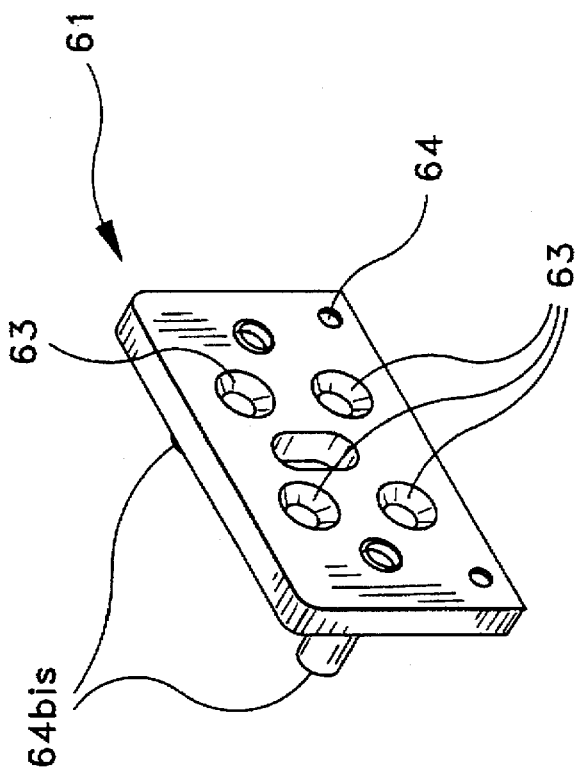
Figure 27:
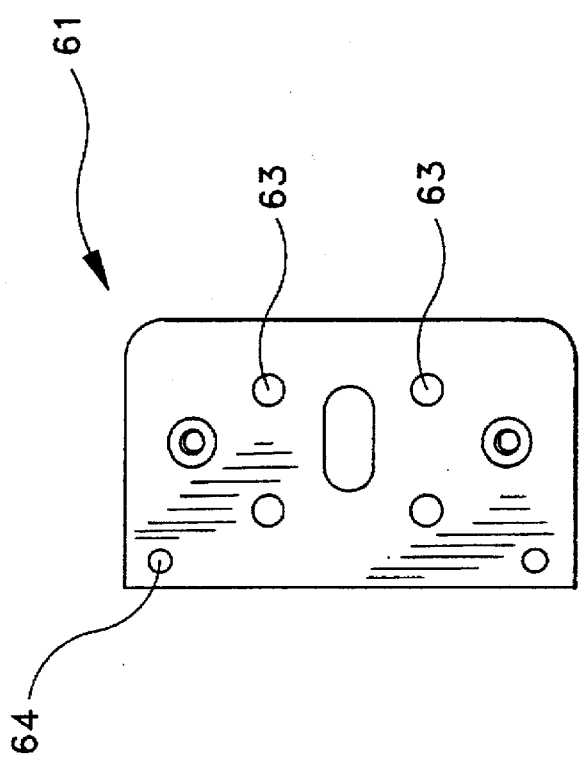

The front face of body 1 is also provided with a vertical groove 27B illustrated in FIG. 10, cooperating with guide pin 8B of the pillar 8 as previously indicated.

As FIGS. 11 to 14 show, each front part 31A or 32A of the upper pair 3 of runners 31 and 32 are each integral with posts 28. Posts 28 is traversed by an axial threaded bore 30.

The calibration arm support 4, with a device for measuring the size of the femoral element, is illustrated in FIGS. 15 to 18; it consists of a base plate 40 comprising a pin 40B and a threaded bore 41 and is integral with two lugs 42, 43 pierced by a bore 44 whose axis is perpendicular to that of the bore 41. Bore 41 is designed to receive the central adjustment screw 41B and bore 44 is designed to accommodate the axis of a bore 46 in a tongue portion 45 of calibration arm 5 which includes a device 51 for measuring the size of the femoral element.

Support 4 cooperates with notch 27 of the central tubular extension 13 when oriented in a direction parallel to the axis of the two pairs of runners of the apparatus and the two lugs 42, 43 which are in the form of a 90° sector, will receive between them the tail 45 of calibration arm 5 with the device described herein below.

Arm 5, equipped with a device for measuring the size of the femoral component, is illustrated in FIGS. 19 to 22. Arm 5 comprises tongue 45 provided with bore 46 and integral with a sleeve 48 comprising at least one bore 50 and whose axis is perpendicular to that of bore 46. Tongue 45 of arm 5 can be inserted between the lugs 42, 43 of the support 4 so as to align their respective bores 44 and 46 and to receive a rotation axis.

In the preferred embodiment, arm 5 can rotate approximately 90° around this axis, and a rigid rod of large size, about 1 meter to 1.5 meters, can be threaded through one of the bores 50 and be immobilized to visibly materialize a direction parallel to the femoro-tibial anatomical axis of the patient and make it possible for the surgeon to verify the hip-knee-ankle alignment, when the apparatus is inserted, through the rear parts of its runners, between the femur and the tibia of the patient with the leg in position of extension.

Extension 48 of arm 5 terminates in a cylindrical element 49. Cylindrical element 49 comprises, in order to measure the size of the prosthetic femoral element, a rigid pin 51 in the form of an inverted U, sliding in two parallel oblique grooves located on the opposite faces of the cylindrical element 49 and displaying reference marks all along a graduation appearing on one of these faces, as illustrated in FIG. 22.

When arm 5 is set on support 4 in the position illustrated in FIG. 1, with the resected extremity of the femur arranged on the front parts 31A and 32A of the upper pair of runners, the surgeon can cause the pin 51 to slide downward until it comes into contact with the anterior cortex extending in the resection plane of the femur. He can then obtain the size of the prosthetic femoral component by reading off the position where the reference marks stopped on the graduation of the cylindrical element (see FIG. 22).

Central adjusting screw 41B, illustrated in FIG. 23, comprises a head integral with a central knurled knob, and the body of the screw exhibits, starting from its head, two successive screw threads 50 and 51 of decreasing diameter separated by a groove 52.

The thread of the end screw 51 cooperates with the threaded bore 11 of the central pillar 8 of spacer 6 and groove 52 with pin 40B of the tubular extension 13, and the arm support 4 and the screw thread 50 is made integral with the central knurled knob.

One of the two identical side screws 53, 54 is illustrated in FIG. 24. It comprises a head integral with a lateral knurled knob, and the body of the screw exhibits, starting from its head, two successive screw threads 55 and 56, of decreasing diameter, separated by a groove 57.

Groove 57 cooperates with the pin 19 or 20 of body 1, the screw thread 56 with the threaded bore 30 of the post 28, and the screw thread 55 is made integral with a knurled knob at the end of the screw.

A retaining plate 61, illustrated in FIGS. 25 to 28 and comprising an oblong hole 62 whose dimensions are analogous to those of oblong holes 12 and 26, perforations 63, 64 and perforated tenons 64B making it possible to position two spindles perpendicularly to the distal femoral cutting plane, is so dimensioned as to enable it to fit perfectly between the walls 38 and 39 of the window 37 of body 1 and to be screwed onto the latter at 36.

Figure 29:
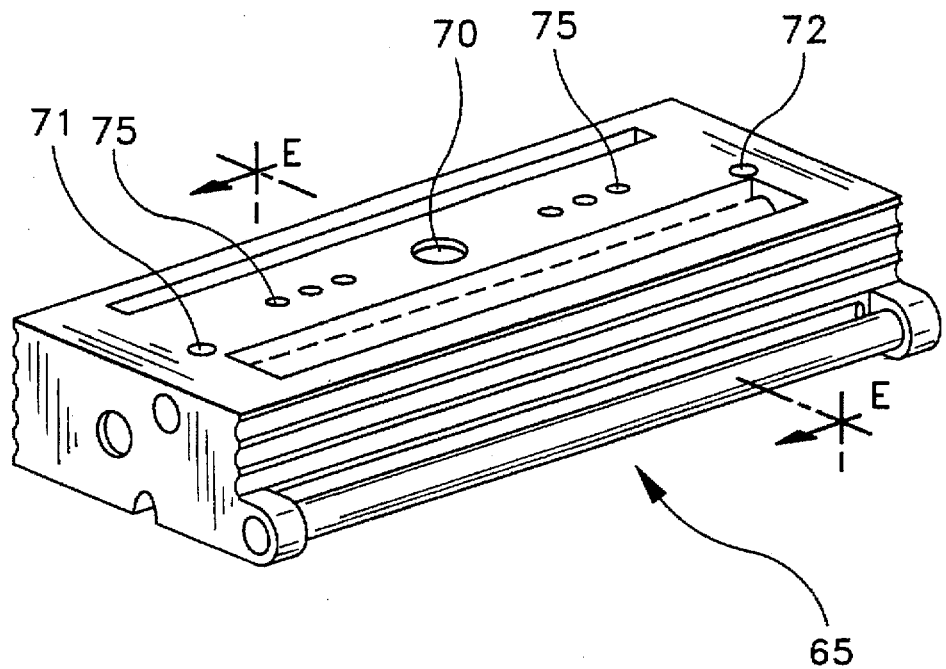
Figure 30:
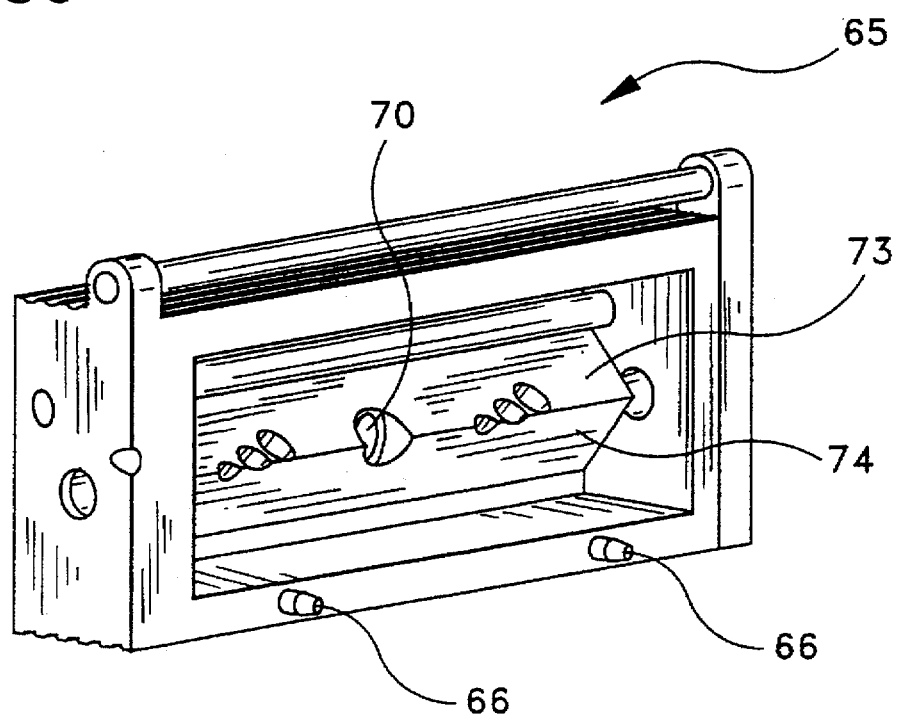

Finally, the apparatus according to the invention can be equipped with an anteroposterior cutting guide 65 illustrated in FIGS. 29 to 31 for use with, for example, an oscillating saw blade.

This anteroposterior cutting guide 65 is presented in the shape of a trapezoidal cross section, the lower and upper surfaces of which are to serve as support for a surgical saw, to define the anterior and posterior cutting planes of the femur with the leg of the patient in flexion.

Cutting guide 65 is provided with positioned device cooperating with those of the body 1. In the preferred embodiment these positioning devices can consist of projections 66 cooperating with the perforations 64 of the retaining plate 61.

The preferred cutting guide 65 can also comprise one or several threaded bores 70, making it possible to fasten it with a suitable tool to body 1 in a recessed position. Guide 65 also has several perpendicular holes 75 corresponding to those placed in the tenons 64B, making it possible to modify the position of the cutting template 65, and one, or preferably two, pairs of bores oriented at an angle of approximately 45° in converging directions from the face comprising the positioning means, as indicated by references 71, 72. Moreover, it can exhibit two planes 73 and 74 inclined at approximately 45° and designed to serve as guide for a surgical saw to execute the chamfers of the resection planes of the femur.

From the above it can be seen that the lower runners 21, 22 are simultaneously mobile and the front parts 31A, 32A of the upper runners 31, 32 are individually mobile, according to a translational motion, in the direction of the axis of the adjusting screws 49, 53 and 54. The rotation of one of the lateral adjusting screws 53, 54, when the cutting guide 65 is in contact with the femur in position of flexion, makes it possible to stabilize and recenter the patella before making the cuts corresponding to this position.

The apparatus thus makes it possible for the surgeon to verify that the spacing of the resected parts between the femur and tibia is the same in position of extension as in position of flexion, and to make sure that the ligament tension is respected and that the centering of the patella is ensured before proceeding with the operations of distal resection of the femur in position of flexion.

We claim:

1. A distraction apparatus for a knee prosthesis, comprising;
    a body having a top pair and a bottom pair of runners arranged one below the other, all parallel to each other and extending in a plane perpendicular to said body so as to form rear extensions on one side of the body, and front extensions on the other side;
    the front extensions and the rear extensions of the lower pair of runners are integral and can be moved simultaneously in relation to the body;
    the front extensions and rear extensions of the upper pair of runners are independent of one another;
    the front extensions of the upper pair of runners can be moved individually in relation to the body; and
    the rear extensions of the upper pair of runners are both integral with the body.

2. The distractor as set forth in claim 1 wherein the front and rear extensions of the lower pair of runners can move simultaneously with respect to the body by the turning of a central adjustment screw mounted on the body, the axis of which is perpendicular to the plane defined by the said runners according to a translational motion in the direction of that axis.

3. The distractor as set forth in claim 1 wherein the front extension of each of the runners of the upper pair can move individually by the turning of a lateral adjustment screw mounted on the body, the axis of which is perpendicular to the plane defined by the said runners according to a translational motion in the direction of that axis.

4. The distractor as set forth in claim 3 wherein the body comprises three screws, the axes of which are perpendicular to the plane defined by the pair of runners, a central adjustment screw for moving said lower pair of runners, and two lateral screws, for moving the front part of the upper pair of runners.

5. The distractor as set forth in claim 4 comprising a central pillar integral with the lower pair of runners, said body integral with the rear extensions of the upper pair of runners, said body being provided with a central bore accepting the central pillar and two lateral bores, each accommodating the passage of adjusting screws.

6. The distractor as set forth in claim 1 further comprising an arm for measuring the size of the femoral element and for indicating the direction of the femoro-tibial axis in the extension position arranged in the center of the body, and means for pivoting said arm along a 90° arc in the orthogonal plane in relation to that of the body and that of the runners.

7. The distractor as set forth in claim 1 further comprising a detachable anteroposterior cutting guide in the shape of a block with a trapezoidal cross section and provided with positioning means to ensure its fixation on the distractor in a specific position and including means for fixing said guide on a resected flat surface of the femur, and means making it possible to define at least one cutting plane by a surgical saw.

8. The distractor as set forth in claim 7 wherein the cutting guide includes a projection and is positioned on the gantry crane by locking said projection into a corresponding recess.

9. The distractor as set forth in claim 8 wherein the fixation means of the cutting guide on a resected flat surface of the femur consists of one or two pairs of bores, preferably inclined at an angle of approximately 45° on a flat face of the cutting guide.

10. The distractor as set forth in claim 9 wherein the means making it possible to define at least one cutting plane for a saw on the cutting guide are its lower surface, and upper surface serving two planes inclined at an angle of approximately 45° to said upper and lower surfaces making it possible to introduce a saw to create chamfers at the distal extremity of the femur.

11. The distractor as set forth in claim 10 wherein the rear extensions of the pair of lower runners have a thickness greater than that of the front extensions of the same pair.

12. The distractor as set forth in claim 11 wherein the rear extensions of the pair of upper runners have a thickness greater than that of the front extensions of the same pair.

13. A distraction apparatus for the knee comprising:

a body having a front and rear face with a pair of runners integrally formed thereon extending from said rear face in a direction generally perpendicular to said rear face of said body;

first and second runners mounted on said body and independently moveable with respect thereto, said first and second runners extending from said front face in a direction generally perpendicular to said front face; and a distraction plate having skids integrally formed thereon extending in the direction perpendicular to both said front and rear faces, said distraction plate mounted on said body and independently moveable thereon with respect to said first and second runners.

14. The distractor as set forth in claim 13 wherein said runners are each mounted on a post slidably received in first and second bores formed in said body.

15. The distractor as set forth in claim 14 wherein said distraction plate is mounted on a post slidably received in a third bore formed in said body.

16. The distractor as set forth in claim 15 wherein said bores are all parallel and said distraction plate post is slidably received in a bore intermediate the bores receiving the posts of said first and second runners.

* * * * *